US011006902B1

(12) United States Patent
Bonyak et al.

(10) Patent No.: US 11,006,902 B1
(45) Date of Patent: May 18, 2021

(54) GUI FOR SELECTIVE OPERATION OF MULTI-ELECTRODE CATHETERS

(71) Applicant: Biosense Webster (Israel) Ltd., Yokneam (IL)

(72) Inventors: Yevgeny Bonyak, Haifa (IL); Michael Levin, Haifa (IL); Eyal Rotman, Kiriat Tivon (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/726,045

(22) Filed: Dec. 23, 2019

(51) Int. Cl.
```
A61B 5/00     (2006.01)
A61B 18/14    (2006.01)
A61B 34/00    (2016.01)
A61B 34/10    (2016.01)
A61B 18/00    (2006.01)
```

(52) U.S. Cl.
CPC ........ A61B 5/7435 (2013.01); A61B 18/1492 (2013.01); A61B 34/25 (2016.02); *A61B 2018/0022* (2013.01); *A61B 2018/00267* (2013.01); *A61B 2018/00577* (2013.01); *A61B 2018/1467* (2013.01); *A61B 2034/104* (2016.02)

(58) Field of Classification Search
CPC ... A61B 5/7435; A61B 18/1492; A61B 34/25; A61B 2018/0022; A61B 2018/00267; A61B 2018/00577; A61B 2034/104; A61B 2018/1467
See application file for complete search history.

(56) References Cited

U.S. PATENT DOCUMENTS

| 5,391,199 A | 2/1995 | Ben-Haim |
| 5,673,695 A * | 10/1997 | McGee ............... A61B 5/0422 |
| | | 600/374 |
| 6,239,724 B1 | 5/2001 | Doron et al. |
| 6,332,089 B1 | 12/2001 | Acker et al. |
| 6,484,118 B1 | 11/2002 | Govari |

(Continued)

FOREIGN PATENT DOCUMENTS

| WO | WO 96/05768 A1 | 2/1996 | |
| WO | WO-2017184628 A1 * | 10/2017 | ............. A63B 34/25 |

OTHER PUBLICATIONS

"Carto 3 System." Instructions for Use. Software Version 4.3. P.N. UG-5400-004H (01D). May 11, 2015. (Year: 2015).*

*Primary Examiner* — Haoshian Shih
*Assistant Examiner* — Alvaro R Calderon, IV

(57) ABSTRACT

A system includes a display, an input device, and a processor. The processor is configured to present to a user, on the display, a GUI that illustrates multiple electrodes disposed on an expandable frame of a multi-electrode catheter, and indicates which of the electrodes is active and which of the electrodes is inactive. The processor is further configured to (a) receive, via the input device first user input that chooses between a single-electrode-selection mode and a fan-selection mode, (b) when in the single-electrode-selection mode, receive via the input device second user input that specifies for activation or deactivation individual ones of the electrodes, and (c) when in the fan-selection mode, receive via the input device third user input that specifies for activation or deactivation an angular sector including two or more of the electrodes, and activate and deactivate the electrodes responsively to the first, second and third user inputs.

19 Claims, 4 Drawing Sheets

(56) References Cited

U.S. PATENT DOCUMENTS

| | | |
|---|---|---|
| 6,618,612 B1 | 9/2003 | Acker et al. |
| 6,625,482 B1 | 9/2003 | Panescu et al. |
| 6,690,963 B2 | 2/2004 | Ben-Haim et al. |
| 7,756,576 B2 | 7/2010 | Levin |
| 7,848,787 B2 | 12/2010 | Osadchy |
| 7,869,865 B2 | 1/2011 | Govari et al. |
| 8,456,182 B2 | 6/2013 | Bar-Tal et al. |
| D774,043 S | 12/2016 | Thompson et al. |
| 2002/0065455 A1 | 5/2002 | Ben-Haim et al. |
| 2002/0068932 A1 | 6/2002 | Edwards et al. |
| 2003/0120150 A1 | 6/2003 | Govari |
| 2004/0068178 A1 | 4/2004 | Govari |
| 2007/0083193 A1 | 4/2007 | Werneth et al. |
| 2007/0180392 A1* | 8/2007 | Russo ............... G06F 3/0482 715/765 |
| 2007/0203545 A1* | 8/2007 | Stone ............ A61N 1/36192 607/59 |
| 2008/0082145 A1 | 4/2008 | Skwarek et al. |
| 2009/0327964 A1* | 12/2009 | Mouilleseaux ....... G06F 3/0482 715/834 |
| 2012/0113039 A1* | 5/2012 | Nghiem ............ G06F 3/04166 345/173 |
| 2014/0371609 A1* | 12/2014 | Narayan .............. A61N 1/327 600/508 |
| 2015/0366476 A1* | 12/2015 | Laughner ........... A61B 5/0422 600/374 |
| 2018/0368927 A1 | 12/2018 | Lyons et al. |
| 2019/0183372 A1* | 6/2019 | Ruppersberg ........ A61B 5/6858 |
| 2020/0163629 A1* | 5/2020 | Dearing ............... A61B 5/743 |

\* cited by examiner

GUI FOR SELECTIVE OPERATION OF MULTI-ELECTRODE CATHETERS

FIELD OF THE INVENTION

The present invention relates generally to controlling medical probes, and particularly to controlling cardiac multi-electrode Electrophysiological (EP) sensing and ablation catheters using a graphical user-interface (GUI).

BACKGROUND OF THE INVENTION

Controlling a tissue ablation process by a probe using a user-interface was previously proposed in the patent literature. For example, U.S. Patent Application Publication 2018/0368927 describes a computer-implemented method for generating and displaying a graphical user interface (GUI). The method includes displaying, via the GUI, a real-time video received from a camera disposed within an ablation catheter. The method further includes displaying, via the GUI, a graphical representation of a plurality of electrodes of the ablation catheter. In an embodiment, one or more controllers in communication with an RF generator and configured to (i) generate a real-time video from the ablation catheter for displaying via the GUI, (ii) generate a graphical representation including electrode icons corresponding to a plurality of electrodes of the ablation catheter for displaying via the GUI, (iii) receive input, via the graphical representation, (iv) selecting at least some of the electrode icons, and (v) cause an RF generator to transmit RF energy to the plurality of electrodes of the ablation catheter corresponding to the selected electrode icons.

As another example, U.S. Pat. No. 6,625,482 describes a GUI for assisting medical personnel in interpreting data collected by a multiple electrode catheter deployed within the body. The GUI generates and displays an image of the multiple electrode catheter. By manipulating appropriate controls, the medical personnel are able to change the orientation of the displayed image until it matches the orientation of the actual multiple electrode catheter as seen on a fluoroscope. Afterwards, the medical personnel can determine the relative position and orientation of the catheter by reference to the GUI generated image. To aid in interpreting data recovered by the catheter, the individual electrodes and splines are highlighted and labeled. Electrodes recovering particular types of physiological waveforms can be automatically identified and highlighted.

U.S. Patent Application Publication 2007/0083193 describes devices, systems and methods for the ablation of tissue. Embodiments include an ablation catheter that has an array of ablation elements including electrodes attached to a deployable carrier assembly, which are configured to ablate tissue at low power. The systems include an interface unit with a visual display that provides a visual representation of the geometry of the ablation elements and/or provides selection means for selecting an icon provided on the display. The user interface may be used to perform numerous functions including but not limited to: selecting electrodes to receive energy, setting power levels, types (bipolar and monopolar) and durations; setting catheter and other system threshold levels, setting mapping and other system parameters, initiating and ceasing power delivery, deactivating an alarm condition, and performing other functions common to electronic medical devices.

SUMMARY OF THE INVENTION

An embodiment of the present invention provides a system including a display, an input device, and a processor, which is configured to present to a user, on the display, a graphical user interface (GUI) that illustrates multiple electrodes disposed on an expandable frame of a multi-electrode catheter, and indicates which of the electrodes is active and which of the electrodes is inactive. The processor is further configured to (a) receive, via the input device first user input that chooses between a single-electrode-selection mode and a fan-selection mode, (b) when in the single-electrode-selection mode, receive via the input device second user input that specifies for activation or deactivation individual ones of the electrodes, and (c) when in the fan-selection mode, receive via the input device third user input that specifies for activation or deactivation an angular sector including two or more of the electrodes, and activate and deactivate the electrodes responsively to the first, second and third user inputs.

In some embodiments, the processor is further configured to automatically update the GUI according to a measured rotational orientation of the expandable frame. In other embodiments, the processor is further is further configured to highlight one of a single-electrode-selection and a fan-selection indication according to the chosen mode.

In an embodiment, the GUI includes an illustration of an expandable balloon catheter. In another embodiment, the GUI includes an illustration of an expandable basket assembly.

In some embodiments, the processor is configured to switch between the single-electrode-selection mode and the fan-selection mode responsively to user clicking on a center area of the GUI.

In some embodiments, in the single-electrode-selection mode, the processor is configured to activate or deactivate an electrode responsively to the user clicking on a GUI element representing the electrode in the GUI.

In other embodiments, in the fan-selection mode, the processor is configured to activate and deactivate the electrodes in the angular sector responsively to the user clicking on a GUI element representing the selected angular sector. In yet other embodiments, in the fan-selection mode, the processor is configured to receive user instructions that perform one or more of widening, narrowing and rotating the angular sector.

There is additionally provided, in accordance with another embodiment of the present invention, a method including presenting to a user, on the display, a graphical user interface (GUI) that illustrates multiple electrodes disposed on an expandable frame of a multi-electrode catheter, and indicates which of the electrodes is active and which of the electrodes is inactive. First user input is received, via an input device, which chooses between a single-electrode-selection mode and a fan-selection mode. When in the single-electrode-selection mode, second user input is received via the input device that specifies for activation or deactivation individual ones of the electrodes. When in the fan-selection mode, third user input is received via the input device that specifies for activation or deactivation an angular sector including two or more of the electrodes. The electrodes are activated and deactivated responsively to the first, second and third user inputs.

There is further provided, in accordance with another embodiment of the present invention, a non-transitory computer-readable medium having stored thereon sequences of instructions which, when executed by a processor, cause the processor to (a) present to a user, on the display, a graphical user interface (GUI) that illustrates multiple electrodes disposed on an expandable frame of a multi-electrode catheter, and indicates which of the electrodes is active and which of the electrodes is inactive, (b) receive, via an input device, first user input that chooses between a single-electrode-selection mode and a fan-selection mode, (c) when in the single-electrode-selection mode, receive via the input device second user input that specifies for activation or deactivation individual ones of the electrodes, (d) when in the fan-selection mode, receive via the input device third user input that specifies for activation or deactivation an angular sector including two or more of the electrodes, and (e) activate and deactivate the electrodes responsively to the first, second and third user inputs.

The present invention will be more fully understood from the following detailed description of the embodiments thereof, taken together with the drawings in which:

DETAILED DESCRIPTION OF EMBODIMENTS

Overview

Figure 1:
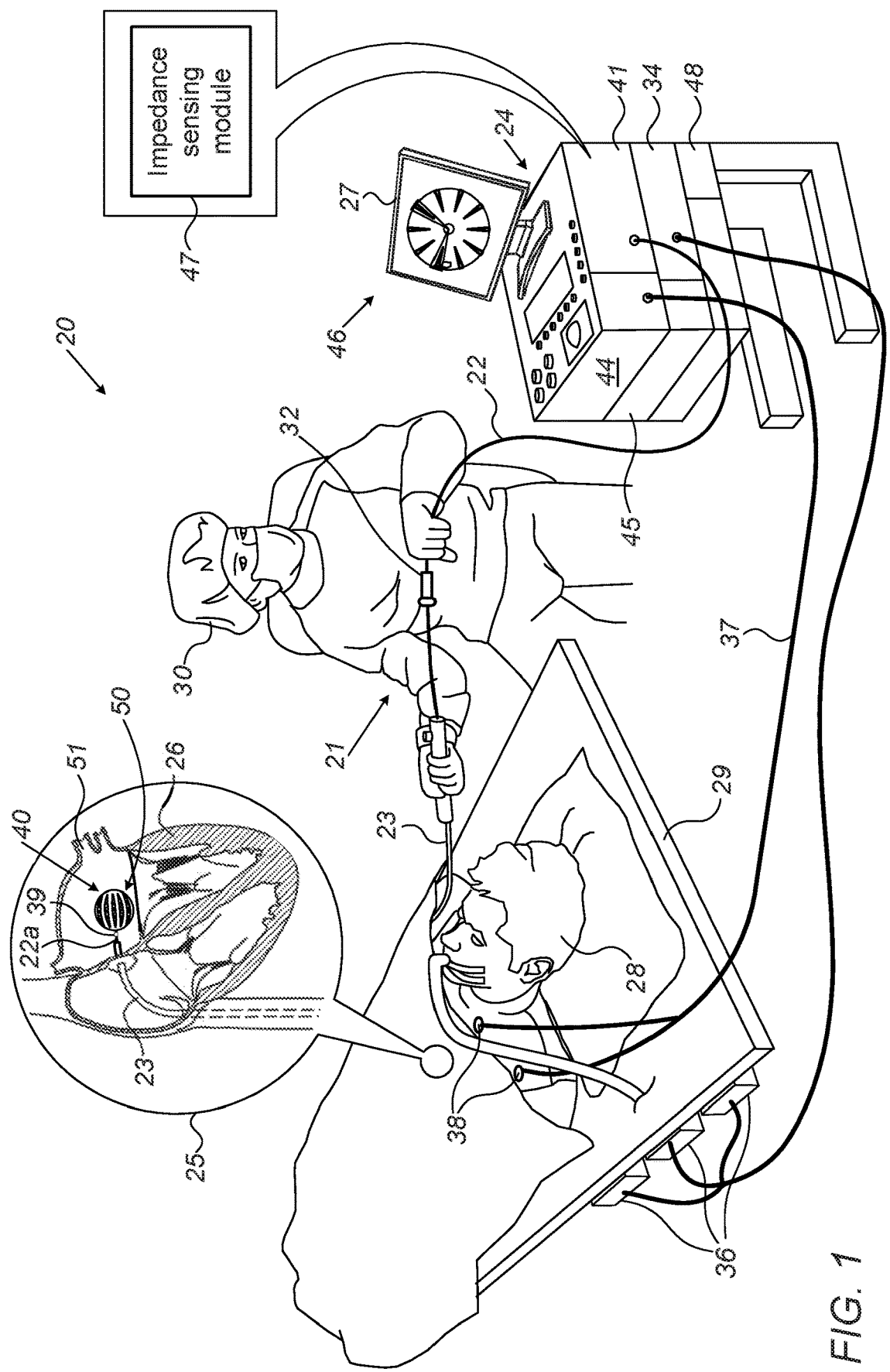
FIG. 1 is a schematic, pictorial illustration of a catheter-based position-tracking and balloon-ablation system comprising a GUI, in accordance with an embodiment of the present invention.

Achieving continuous and comprehensive physician awareness, and physician control, of multiple possible permutations of electrode configuration of a medical probe, e.g., for safe multi-electrode ablation, is challenging.

For example, a physician may use a catheter having an expandable frame (e.g., balloon or basket) fitted at its distal end and disposed with the multiple electrodes, and it is important that the ablating electrodes do not cause collateral damage during ablation. Specifically, based on a received indication, such as a potential hazard if one or more of the electrodes is operated for ablation, a physician who performs the ablation may want to disable one or more electrodes. In some cases, the physician may want to disable a group of neighboring electrodes.

For example, in case of pulmonary vein isolation, the physician may receive an indication that some of the electrodes on the expandable frame are located such that, if operated for ablation, they may cause collateral damage to sensitive tissue (e.g., to the phrenic nerve or esophageal tissue). As another example, the physician may receive an indication that some of the electrodes have insufficient contact with cardiac tissue and therefore, if operated for ablation, may, in some cases, form blood clots. In view of the above complicated scenarios that involve potential hazards, a physician may benefit from a visual input of the updated enabled/disabled configuration of the ablation electrodes and to readily act upon them to optimize such a configuration.

As yet another example, a physician may want to selectively use a partial set of electrodes to sense electrophysiological signals of importance and avoid collecting irrelevant signals from other electrodes, such as from electrodes immersed in a blood pool of a cardiac chamber. For that as well the physician may benefit from a visual input of the updated enabled/disabled configuration of the relevant/irrelevant electrodes.

Embodiments of the present invention that are described hereinafter provide techniques to assist a physician to be aware of and to readily control multiple permutations of electrode configuration of a medical probe, for example, in order to plan and apply ablation in a spatially selectable manner, and thus ensure safe ablation. The disclosed embodiments provide the physician with a graphical user interface (GUI) that lets the physician select and adjust an operational configuration of the multiple electrodes by enabling and disabling an individual electrode or a group of electrodes. The physician can optimize the operational configuration according to indications received before and during the ablation session.

In some embodiments, the disclosed GUI illustrates a front view of the expandable frame (e.g., a balloon) including an illustration of the electrodes and their listing in numerical sequence, e.g., #1, #2, . . . #9, #10. The GUI further provides a single electrode selection mode, in which clicking on any given electrode (using a mouse or touch display or other suitable input device) toggles the electrode between ablation-enabled and ablation-disabled states.

Furthermore, by clicking in a center area of the illustrated frame, the user can toggle between a single electrode selection mode and a fan selection mode. In the fan selection mode, an angular section (i.e., a "fan" or "sector") selected covers, by default, multiple (e.g., three) electrodes. Once selected, the angular section is highlighted or emphasized in another graphical way. The position of the fan can be changed using a suitable input device such as a mouse or a touch display. In addition, one click using the input device can enable/disable the group of electrodes. In the fan selection mode, the user may rotate a selected (e.g., highlighted) section, widen the selected section to include more electrodes, or narrow the highlighted section to include fewer electrodes. The widening or narrowing can be performed from any of the two borders of the angular section, or, on a touch display, symmetrically using a two-finger gesture.

In some embodiments, a system is provided that includes a display, an input device, and a processor, which is configured to: (a) present to a user, on the display, a graphical user interface (GUI) that illustrates multiple electrodes disposed on an expandable frame of a multi-electrode catheter, and indicates which of the electrodes is active and which of the electrodes is inactive, (b) receive, via the input device, first user input that chooses between a single-electrode-selection mode and a fan-selection mode, (c) when in the single-electrode-selection mode, receive via the input device second user input that specifies for activation or deactivation individual ones of the electrodes, (d) when in the fan-selection mode, receive via the input device third user input that specifies for activation or deactivation an angular sector comprising two or more of the electrodes; and, (e) activate and deactivate the electrodes responsively to the first, second and third user inputs.

During an ablation procedure the expandable frame (e.g., balloon or basket) may be rotated in the organ, intentionally or unintentionally. The rotation may be detected, as described below, and the sequence of disabled electrodes shown on a display may be changed automatically to compensate for the rotation, for example from #10, #1, #2 to #1, #2, #3. In other words, upon detecting rotation of the expandable frame, the processor may modify the subset of electrodes that are active/inactive to compensate for the rotation.

Typically, the processor is programmed in software containing a particular algorithm that enables the processor to conduct each of the processor-related steps and functions outlined above.

By providing the disclosed GUI, a spatially selective multi-electrode ablation technique using the GUI can be readily used by a physician, thereby providing safer multi-electrode ablation treatments.

SYSTEM DESCRIPTION

FIG. 1 is a schematic, pictorial illustration of a catheter-based position-tracking and balloon-ablation system 20 comprising a GUI 46, in accordance with an embodiment of the present invention. System 20 comprises a catheter 21 that is fitted at a distal end 22a of a shaft 22 of the catheter with an RF ablation expandable balloon 40 comprising multiple electrodes 50 (seen in inset 25). In the embodiment described herein, electrodes 50 are used to ablate tissue of an ostium 51 of a PV in a heart 26.

The proximal end of catheter 21 is connected to a control console 24 comprising an ablative power source 45. Console 24 includes a processor 41 that presents GUI 46, wherein a user can operate GUI 46, for example, from a touch display 27, to allow a physician to see an illustration of balloon 40 and electrodes 50, and to enable or disable one or more electrodes 50 as ablation electrodes using the disclosed GUI 46 tools, as described in FIG. 3. In an embodiment, touch display 27 also serves as an input device for receiving user input. Additionally or alternatively, any other suitable input device, such as a mouse, trackball or keyboard, can be used.

An ablation protocol comprising ablation parameters including criteria against which an indication from electrodes 50 is compared by processor 41 or a physician 30, to decide to enable or disable an electrode, is stored in a memory 48 of console 24.

Physician 30 inserts distal end 22a of shaft 22 through a sheath 23 into heart 26 of a patient 28 lying on a table 29. Physician 30 advances the distal end of shaft 22 to a target location in heart 26 by manipulating shaft 22 using a manipulator 32 near the proximal end of the catheter and/or deflection from the sheath 23. During the insertion of distal end 22a, balloon 40 is maintained in a collapsed configuration by sheath 23. By containing balloon 40 in a collapsed configuration, sheath 23 also serves to minimize vascular trauma along the way to target location.

Once distal end 22a of shaft 22 has reached heart 26, physician 30 retracts sheath 23 and partially inflates balloon 40, and further manipulates shaft 22 to navigate balloon 40 to an ostium 51 the pulmonary vein.

In an embodiment, physician 30 navigates the distal end of shaft 22 to the target location by tracking a position of balloon 40 using impedances measured between electrodes 50 and surface electrodes 38.

To perform its functions, processor 41 includes an electrode impedance sensing module 47. In the exemplified system, impedance-sensing module 47 receives electrical impedance signals, measured between electrodes 50 and surface electrodes 38, which are seen as attached by wires running through a cable 37 to the chest of patient 28. Electrodes 50 are connected by wires running through shaft 22 to processor 41 controlling interface circuits 44 in a console 24.

A method for tracking the positions of electrodes, such as electrodes 50, using the aforementioned measured impedances is implemented in various medical applications, for example in the CARTO™ system, produced by Biosense-Webster (Irvine, Calif.) and is described in detail in U.S. Pat. Nos. 7,756,576, 7,869,865, 7,848,787, and 8,456,182, whose disclosures are all incorporated herein by reference with a copy provided herein the Appendix. This method is sometimes called Advanced Catheter Location (ACL). In an embodiment, console 24 drives a display 27, which shows the tracked position of balloon 40 inside heart 26.

When at target position (e.g., at ostium 51), physician 30 fully inflates balloon 40 and places electrodes 50 disposed equidistantly over an entire perimeter of balloon 40 in contact with ostium 51 tissue.

Next, in some embodiments, physician 30 measures, e.g., using impedance sensing module 47, impedance of each of the electrodes, as described above. Processor 41 compares the measured impedance of each electrode with a preset threshold. If electrode impedance is below or equals the preset impedance threshold, meaning that the electrode is in contact with blood rather than being in good contact with tissue, processor 41 indicates this on GUI 46 on display 27 to disable the electrode. If, on the other hand, the electrode impedance is above the preset threshold, meaning that the electrode is in good contact with tissue, the processor presents the electrode by the GUI as an enabled ablation electrode. In another embodiment, processor 41 may update GUI 46 to indicate electrodes having locations in proximity to sensitive tissue in the vicinity of ostium 51.

In other embodiments, system 20 provides an indication on the GUI regarding electrodes 50, such as their locations relative to sensitive tissue, such as the esophagus or a nerve, to assist the physician to decide which electrode or group of electrodes to disable.

As further shown in inset 25, distal end 22a comprises a magnetic position sensor 39 contained within distal end 22a just proximally to expandable balloon 40. During navigation of distal end 22a in heart 26, console 24 receives signals from magnetic sensor 39 in response to magnetic fields from external field generators 36, for example, for the purpose of measuring the direction and angular orientation of ablation balloon 40 in the heart and, as described above, presenting the tracked information on display 27. Magnetic field generators 36 are placed at known positions external to patient 28, e.g., below patient table 29. Console 24 also comprises a driver circuit 34, configured to drive magnetic field generators 36.

The method of direction sensing using external magnetic fields is implemented in various medical applications, for example, in the CARTO™ system, produced by Biosense-Webster and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference with a copy provided in the Appendix.

In an embodiment, signals from sensor 39 are further used for position sensing using the aforementioned CARTO™ system.

Processor 41 is typically a general-purpose computer, with suitable front end and interface circuits 44 for receiving signals from catheter 21, as well as for applying RF energy treatment via catheter 21 in a left atrium of heart 26 and for controlling the other components of system 20. Processor 41 typically comprises a software in a memory 48 of system 20, which is programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, included in FIG. 4, which enables processor 41 to perform the disclosed steps, as further described below.

While FIG. 1 describes a multi-electrode balloon catheter, the principles of the present technique apply to any catheter having a distal end fitted with multiple electrodes, such as the aforementioned Lasso and basket catheters.

GUI for Selective Operation of Multi-Electrode Catheters

Figure 2:
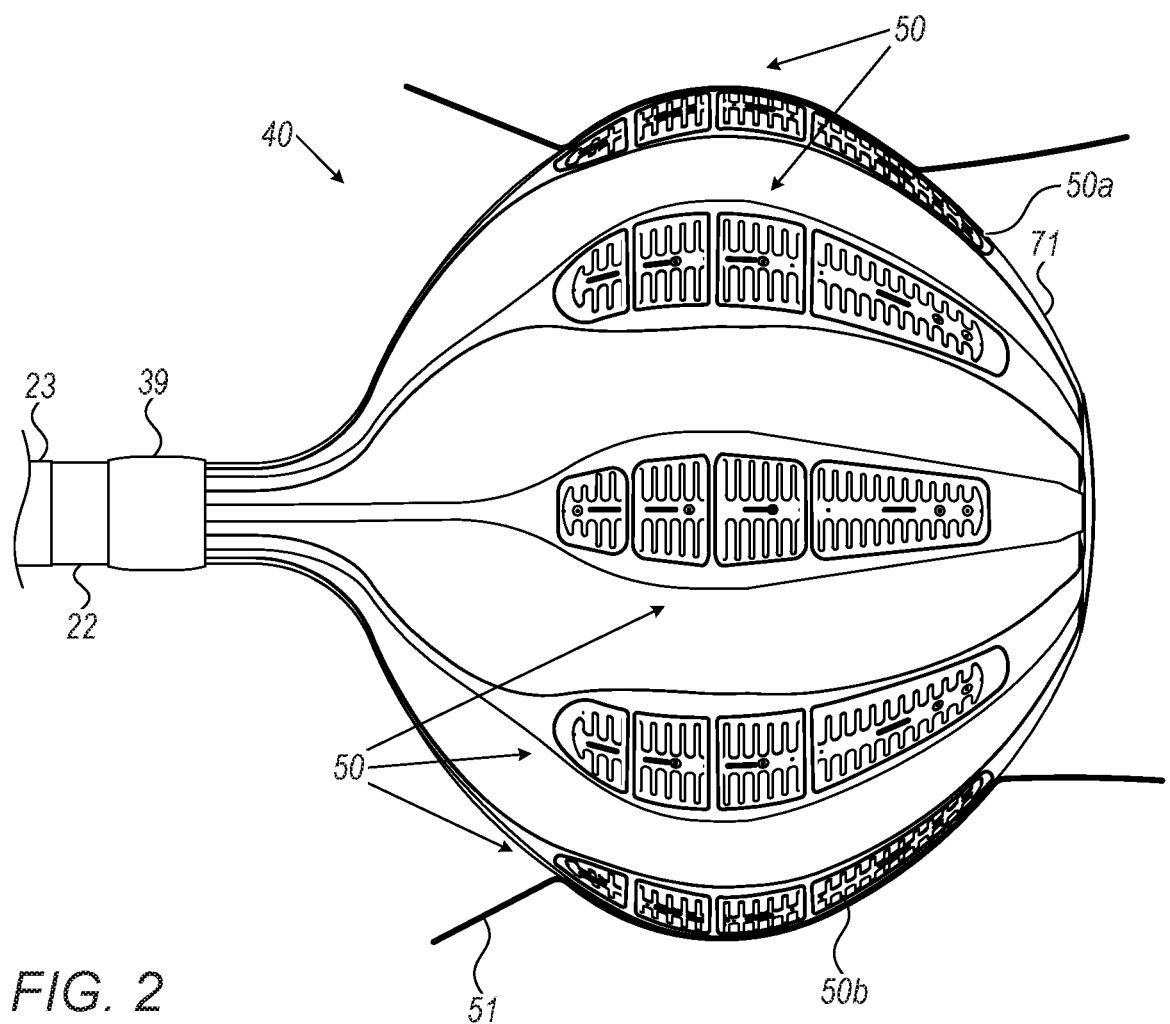
FIG. 2 is a schematic, pictorial side view of a distal end of the balloon catheter of FIG. 1 deployed in a region of a pulmonary vein (PV) and its ostium, in accordance with an embodiment of the invention.

FIG. 2 is a schematic, pictorial side view of the balloon catheter of FIG. 1 deployed in a region of a pulmonary vein (PV) and its ostium 51, in accordance with an embodiment of the invention. The balloon catheter is used to ablate ostium 51 tissue to isolate a source of arrhythmia. Balloon 40 has ten electrodes 50 disposed over a membrane 71 of the balloon. Electrical power can be delivered from ablative power source 45 independently to each of the ten electrodes 50, depending on the level of physical contact of each electrode 50 with tissue during ablation.

As seen in FIG. 2, an electrode 50a is not in good contact with tissue. Based on impedance readings from electrode 50a as below or equal to the preset impedance value, processor 41 determines the insufficient physical contact of electrode 50a. Accordingly, processor 41 indicates this on GUI 46 on display 27 so that physician 30 may disable electrode 50a.

An electrode 50b, on the other hand, is in good contact with tissue. Based on impedance readings from electrode 50b as above the preset threshold impedance value, processor 41 determines the sufficient physical contact of electrode 50b. Accordingly, processor 41 may indicate on GUI 46 on display 27 that ablation electrode 50b is enabled.

The pictorial side view shown in FIG. 2 is chosen by way of example, where other embodiments are possible. For example, in another embodiment, a group of electrodes 50 may be shown lacking sufficient contact with tissue.

Figure 3:
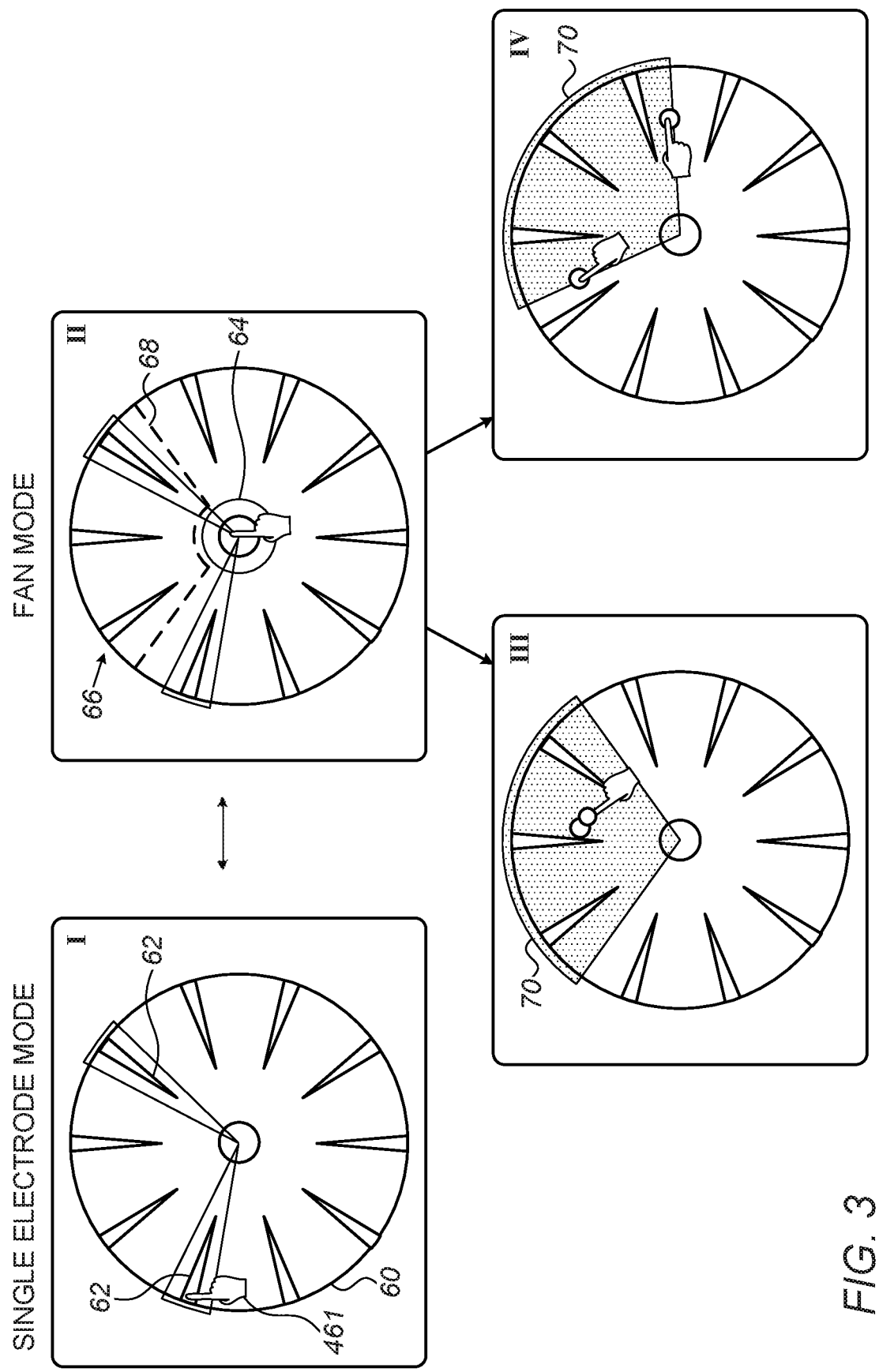
FIG. 3 is a schematic, pictorial illustration of the GUI of FIG. 1, in accordance with some embodiments of the invention.

FIG. 3 is a schematic, pictorial illustration of GUI 46 of FIG. 1, in accordance with some embodiments of the invention. Box I of FIG. 3 shows how GUI 46 illustrates (60) balloon 40 using a front view of the balloon including an illustration (62) of electrodes 50 including their listing in numerical sequence, e.g., #1, #2, . . . #9, #10.

Block I shows the single electrode selection mode, in which a user clicking (461) on any given electrode toggles the electrode between an enabled and a disabled state. Once selected, the electrode is highlighted or emphasized in another graphical way.

Box II of FIG. 3 shows how a user can toggle to fan mode by clicking in the center area 64 of the balloon to toggle between the fan mode, illustrated by dashed section 68, and the single electrode mode. Once selected, the angular section is highlighted or emphasized in another graphical way. As seen, section 68 includes a group 66 of neighboring electrodes. In the fan mode the size (typically set at a default of three electrodes) and position of the fan can be changed using a suitable input device such as a mouse or the touch display. In addition, one click can enable/disable any group of electrodes over the perimeter, according to where the user clicks in area 64 (e.g., top part or bottom part, and left part or right part).

Block III illustrates the GUI tool of the fan mode, which enables the user to rotate a selected section 70. Block IV illustrates another GUI tool of the fan mode, which enables the user to widen a selected section 70 to have more electrodes disabled or to narrow section 70 to have fewer electrodes disabled. The widening or narrowing can be performed from any of the two borders of the section, or, in a touch display, symmetrically using a two-finger gesture.

During an ablation procedure balloon 40 may be rotated intentionally or unintentionally. The rotation may be detected by the aforementioned CARTO system, and the sequence of disabled electrodes may be changed automatically to compensate for the rotation, for example from #10, #1, #2 to #1, #2, #3.

Figure 4:
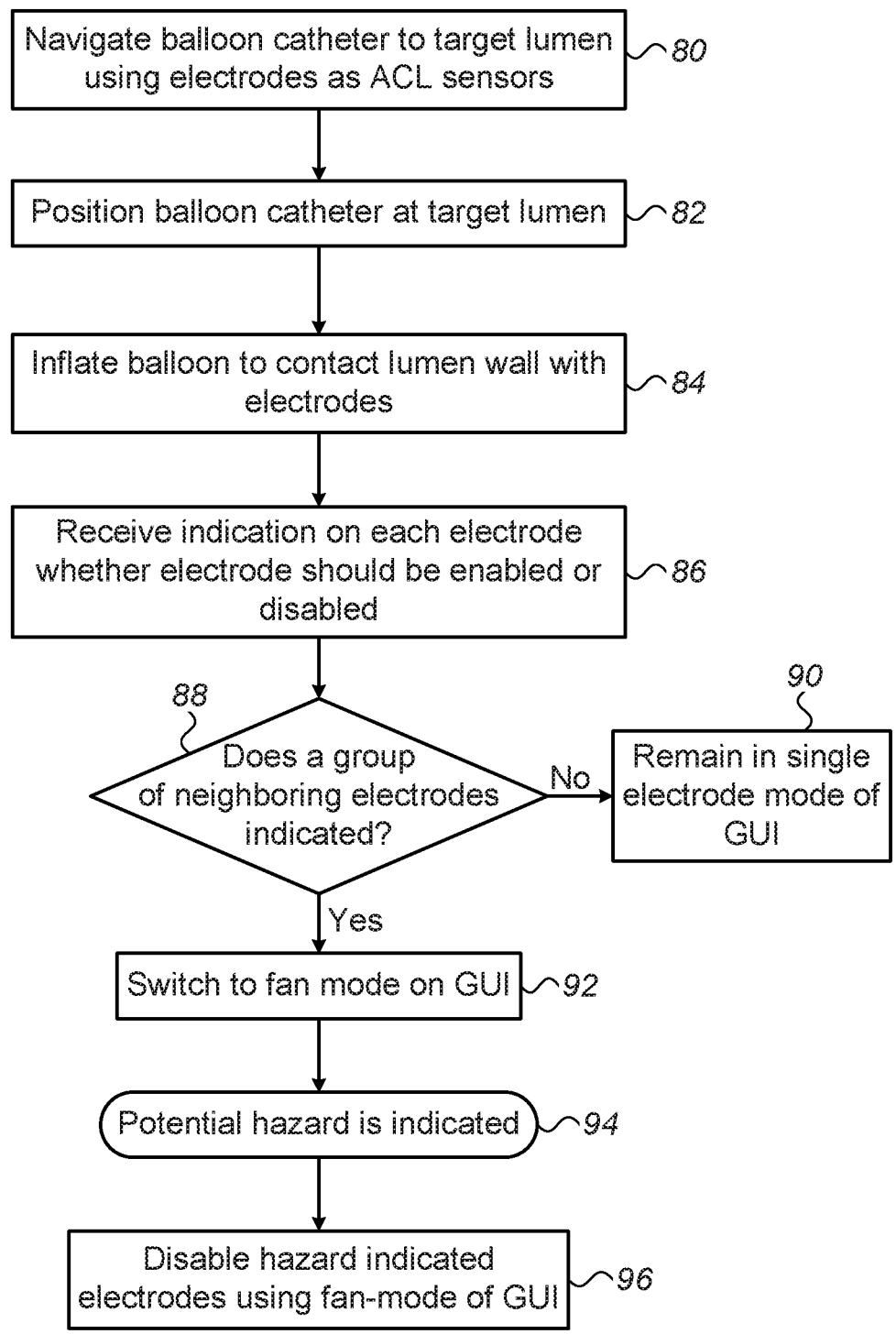
FIG. 4 is a flow chart that schematically illustrates a method for using the GUI of FIG. 3, in accordance with an embodiment of the invention.

FIG. 4 is a flow chart that schematically illustrates a method for using GUI 46 of FIG. 3, in accordance with an embodiment of the invention. The algorithm, according to the presented embodiment, carries out a process that begins when physician 30 navigates the balloon catheter to a target location within a lumen of a patient, such as at ostium 51, using, for example, electrode 50 as ACL-sensing electrodes, at a balloon catheter navigation step 80.

Next, physician 30 positions the balloon catheter at ostium 51, at a balloon catheter positioning step 82. Next, physician 30 fully inflates balloon 40 to contact the lumen wall with electrodes 50 over an entire circumference of the lumen, at a balloon inflation step 84.

Next, physician 30 receives an indication regarding, for example, the location and sufficiency of physical contact of each electrode 50 with tissue, at an electrode indication step 86.

For example, the system may indicate, using impedance sensing module 47 as described above, that one or more electrodes are in contact with blood rather than being in good contact with tissue, and subsequently processor 41 updates GUI 46 to indicate that the electrode or the group of electrodes should be disabled from use as ablation electrodes, as described below.

At an electrode configuration step 88, processor 41 checks if an isolated electrode or a group of neighboring electrodes is indicated. If an isolated electrode is indicated, processor 41 maintains GUI 46 in single electrode mode, in a mode selection step 90. Based on the indication, the physician may disable the electrode, as described in Box I of FIG. 3.

If a group of neighboring electrodes is indicated, processor 41 switches GUI 46 into fan mode, in a mode toggling step 92. Assuming, based on the indication, that a hazard (e.g., of collateral damage to tissue or of blood clots) is indicated (94), the physician disables the indicated group of electrodes, using the fan mode as described above, in an electrode group disablement step 96.

The example flow chart shown in FIG. 4 is chosen purely for the sake of conceptual clarity. In alternative embodiments, additional steps may take place, such as an automatic rotation of an indicated section to compensate for catheter rotation.

While FIG. 4 describes a multi-electrode balloon catheter, the principles of the present technique apply to any catheter having a distal end fitted with multiple electrodes, such as the aforementioned basket catheter.

Although the embodiments described herein mainly address pulmonary vein isolation, the methods and systems described herein can also be used in other applications that require a determination of occlusion, such as, for example, renal denervation, and generally, in ablating other organs.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
a display;
an input device; and
a processor, configured to:
present to a user, on the display, a graphical user interface (GUI) that illustrates a front view of multiple electrodes disposed radially about a center of a circular frame representative of a multi-electrode expandable catheter, and indicates which of the electrodes is active and which of the electrodes is inactive;
receive, via the input device, first user input that chooses between a single-electrode-selection mode and a fan-selection mode;
when in the single-electrode-selection mode, receive via the input device second user input that specifies one of activation or deactivation individual ones of the electrodes;
when in the fan-selection mode, receive via the input device third user input that specifies one of activation or deactivation of an angular sector comprising two or more of the electrodes;
subsequently activate or deactivate the electrodes responsively to the third user input; and
upon detection of rotation of the expandable frame about the center, automatically change the activation or deactivation of the two or more of the electrodes in the angular sector represented in the GUI to different electrodes that are now in the angular sector due to rotation of the expandable frame about its center.

2. The system according to claim 1, wherein the processor is further configured to automatically update the GUI according to a measured rotational orientation of the expandable frame.

3. The system according to claim 1, wherein the processor is further is further configured to highlight one of a single-electrode-selection and a fan-selection indication according to the chosen mode.

4. The system according to claim 1, wherein the GUI comprises an illustration of an expandable balloon catheter.

5. The system according to claim 1, wherein the GUI comprises an illustration of an expandable basket assembly.

6. The system according to claim 1, wherein the processor is configured to switch between the single-electrode-selection mode and the fan-selection mode responsively to user clicking on a center area of the circular frame represented by the GUI.

7. The system according to claim 1, wherein, in the single-electrode-selection mode, the processor is configured to activate or deactivate an electrode responsively to the user clicking on a GUI element representing the electrode in the GUI.

8. The system according to claim 1, wherein, in the fan-selection mode, the processor is configured to activate and deactivate the electrodes in the angular sector responsively to the user clicking on a GUI element representing the selected angular sector.

9. The system according to claim 1, wherein, in the fan-selection mode, the processor is configured to receive user instructions that perform one or more of widening, narrowing and rotating the angular sector.

10. A method, comprising:
presenting to a user, on the display, a graphical user interface (GUI) that illustrates multiple electrodes disposed radially about a center of a circular frame representative of a multi-electrode expandable catheter, and indicates which of the electrodes is active and which of the electrodes is inactive;
receiving, via an input device, first user input that chooses between a single-electrode-selection mode and a fan-selection mode;
when in the single-electrode-selection mode, receiving via the input device second user input that specifies one of activation or deactivation of individual ones of the electrodes;
when in the fan-selection mode, receiving via the input device third user input that specifies one of activation or deactivation of an angular sector comprising two or more of the electrodes; and
activating or deactivating the electrodes responsively to the third user input,
upon detection of rotation of the expandable frame about the center, changing the activation or deactivation of the two or more of the electrodes in the angular sector represented in the GUI to different electrodes of the circular expandable frame that are now in the angular sector represented by the GUI due to rotation of the circular frame about its center.

11. The method according to claim 10, and comprising automatically updating the GUI according to a measured rotational orientation of the expandable frame.

12. The method according to claim 10, and comprising highlighting one of a single-electrode-selection and a fan-selection indication according to the chosen mode.

13. The method according to claim 10, wherein presenting the GUI comprises presenting an illustration of an expandable balloon catheter.

14. The method according to claim 10, wherein presenting the GUI comprises presenting an illustration of an expandable basket assembly.

15. The method according to claim 10, and comprising switching between the single-electrode-selection mode and the fan-selection mode responsively to the user clicking on a center area of the circular frame represented by the GUI.

16. The method according to claim 10, wherein, in the single-electrode-selection mode, activating or deactivating an electrode comprises responding to the user clicking on a GUI element representing the electrode in the GUI.

17. The method according to claim 10, wherein, in the fan-selection mode, activating and deactivating the electrodes in the angular sector comprises responding to the user clicking on a GUI element representing the selected angular sector.

18. The method according to claim 10, wherein, in the fan-selection mode, receiving the third user input comprises receiving user instructions that perform one or more of widening, narrowing and rotating the angular sector.

19. A non-transitory computer-readable medium having stored thereon sequences of instructions which, when executed by a processor, cause the processor to:
- present to a user, on the display, a graphical user interface (GUI) that illustrates multiple electrodes disposed radially about a center of a circular frame representative of a multi-electrode expandable catheter, and indicates which of the electrodes is active and which of the electrodes is inactive;
- receive, via an input device, first user input that chooses between a single-electrode-selection mode and a fan-selection mode;
- when in the single-electrode-selection mode, receive via the input device second user input that specifies one of activation or deactivation of individual ones of the electrodes;
- when in the fan-selection mode, receive via the input device third user input that specifies one of activation or deactivation of an angular sector comprising two or more of the electrodes;
- activate and deactivate the electrodes responsively to the third user inputs; and
- upon detection of the circular expandable frame about its center, automatically change the activation or deactivation of the two or more of the electrodes in the angular sector represented by the GUI to different electrodes that are now in the angular sector due to rotation of the circular expandable frame.

\* \* \* \* \*